United States Patent [19]

Gardner et al.

[11] Patent Number: 5,980,951
[45] Date of Patent: Nov. 9, 1999

[54] ORAL COATED ACTIVE DRUGS

[75] Inventors: Colin R. Gardner, Blue Bell; Mandana Asgharnejad, Lansdale, both of Pa.

[73] Assignee: Merck & Co., Inc., Rahway, N.J.

[21] Appl. No.: 08/833,702

[22] Filed: Apr. 8, 1997

Related U.S. Application Data

[60] Provisional application No. 60/015,176, Apr. 10, 1996, and provisional application No. 60/023,999, Aug. 12, 1996.

[51] Int. Cl.⁶ .............................. A61K 9/16; A61K 9/50
[52] U.S. Cl. ..................... 424/490; 424/489; 424/494; 424/486; 424/487; 424/464
[58] Field of Search .................................. 514/317, 340, 514/212; 424/490, 489, 494, 486, 487, 464; 546/335

[56] References Cited

U.S. PATENT DOCUMENTS

| | | | |
|---|---|---|---|
| 3,689,634 | 9/1972 | Kliment et al. | 424/21 |
| 4,976,949 | 12/1990 | Meyer et al. | 424/468 |
| 5,171,580 | 12/1992 | Iamartino et al. | 424/490 |
| 5,206,373 | 4/1993 | Chung et al. | 546/335 |
| 5,227,490 | 7/1993 | Hartman et al. | 514/317 |
| 5,374,430 | 12/1994 | Newton et al. | 424/458 |
| 5,446,056 | 8/1995 | Wityak et al. | 514/340 |
| 5,470,849 | 11/1995 | Callahan et al. | 514/212 |

OTHER PUBLICATIONS

Lui et al., Journal of Pharmaceutical Sciences, "Application of a Radiotelemetric System to Evaluate the . . . ", vol. 75, No. 5, pp. 469–474 (1986).

Dressman et al., Journal of Pharmaceutical Sciences, "Radiotelemetric Mehod for Evaluating Enteric Coatings in Vivo", vol. 73, No. 7, pp. 935–938 (1984).

Chan et al., Pharmaceutical Research, "Application of Radiotelemetric Technique in Evaluating Diclofenac Sodium. . .", vol. 7, No. 10, pp.. 1026–1032 (1990).

Mojaverian et al., Pharmaceutical Research, "Mechanism of Gastric Emptying of a Nondisintegrating. . . ", vol. 8, No. 1, pp. 97–98 (1991).

Mojaverian et al., Gastroenterology "Estimation of Gastric Residence Time of the Heidelberg Capsule . . . ", vol. 89, pp. 392–397 (1985).

Russell et al., aaps American Association of Pharmaceutical Scientists, "Upper Gasrointestinal PH in 80 Healty, Older Subjects . . . ", Abstract Reproduction Form, (1991).

Dressman, Pharmaceutical Research, "Upper Gastrointestinal (GI) pH in Young, Healthy Men and Woman", vol. 7, No. 7, pp. 756–761 (1990).

*Primary Examiner*—Thurman K. Page
*Assistant Examiner*—William E. Benston, Jr.
*Attorney, Agent, or Firm*—Richard S. Parr; Melvin Winokur

[57] ABSTRACT

An oral drug dosage unit, for administration to a patient, having active drug, and an effective diameter and surface composition sufficient for the unit to be transported from the stomach into the duodenum following substantially complete emptying of chyme from the stomach into the intestine and prior to release of active drug from the unit, wherein the active drug has an absorption rate that is substantially affected by the coinciding presence of food in the stomach, the effective diameter of the unit prevents gastric emptying of the unit prior to gastric emptying of chyme, and the surface composition is an enteric coating which prevents release of the active drug in the stomach and allows release of the active drug in the intestine.

8 Claims, No Drawings

ORAL COATED ACTIVE DRUGS

Verified provisional application No. 60/015,176 filed Apr. 10, 1996 and No. 60/023,999 filed Aug. 12, 1996.

BACKGROUND OF THE INVENTION

The present invention relates to a coated so active drug composition having releasability of the active drug in the small or large intestine or, more particularly, to a coated solid fibrinogen receptor antagonist composition which, when orally administered, passes unaffected through the stomach but is disintegrated when it reaches the small or large intestine so as to release the therapeutically active drug contained therein only in the small or large intestine.

Platelet activation and aggregation are involved in unstable angina and acute myocardial infarction, in reocclusion following thrombolytic therapy and angioplasty, in transient ischemic attacks and in a variety of other vasoocclusive disorders. When a blood vessel is damaged either by acute intervention such as angioplasty, or, more chronically, by the pathophysiological processes of atherosclerosis, platelets are activated to adhere to the disrupted surface and to each other. This activation, adherence and aggregation may lead to occlusive thrombus formation in the lumen of the blood vessel.

Antiplatelet therapy has been used in a wide variety of cardiovascular disease states and in conjunction with interventional therapy such as coronary artery or peripheral bypass grafting, cardiac valve replacement, and percutaneous transluminal coronary angioplasty (PTCA). Available drugs, such as aspirin and ticlopidine, have shown efficacy in syndromes involving vascular occlusion, presumably due to sustained inhibition of platelet function. However, the inhibitory effects of aspirin and ticlopidine are dependent upon the agonist which activates the platelet. For example, aspirin is effective in blocking platelet aggregation induced by agonists such as collagen that are dependent upon the cylooxygenase pathway. It is, however, less effective against concentrations of thrombin which can act by cyclooxygenase independent pathways. Likewise, ticlopidine's inhibitory effects can be overcome by combinations of agonists. Thus, an efficacious inhibitor of platelet aggregation that acts independently of the agonist and the pathway activating the platelet could be an important therapeutic advance providing greater efficacy than aspirin or ticlopidine in a broader spectrum of thrombotic events.

The final obligatory step in platelet aggregation is the binding of fibrinogen to an activated membrane-bound glycoprotein complex, GP IIb/IIIa ($\alpha_{II}\beta_3$). Platelet activators such as thrombin, collagen, epinephrine or ADP, are generated as an outgrowth of tissue damage. During activation, GP IIb/IIIa undergoes changes in conformation that results in exposure of occult binding sites for fibrinogen. There are six putative recognition sites within fibrinogen for GP IIb/IIIa and thus fibrinogen can potentially act as a hexavalent ligand to crossing GP IIb/IIIa molecules on adjacent platelets. A deficiency in either fibrinogen or GP IIb/IIIa prevents normal platelet aggregation regardless of the agonist used to activate the platelets. Since the binding of fibrinogen to its platelet receptor is an obligatory component of normal aggregation, GP IIb/IIIa is an attractive target for an antithrombotic agent.

Orally active agents include SC54684, which is a prodrug (i.e., it requires biotransformation in vivo to its active form) with high oral bioavailability and RO43-8857, GR144053, and DMP728, which are themselves the active inhibitors (Cook et al. ibid.; and Cox et al. ibid.). Literally thousands of other compounds have been synthesized in an attempt to obtain optimal potency, metabolic stability, receptor specificity, and favorable intravascular survival. Despite variations in these compounds, virtually all of them retain the basic charge relations of the RGD sequence with a positive charge separated from a negative charge by approximately 10–20 Å (Cook et al. ibid.; and Cox et al. ibid.). Acad. ibid.).

Oral fibrinogen receptor antagonists are readily absorbed when a patient consumes them on an empty stomach. However, it has been recently observed that absorption and bioavailability of oral fibrinogen receptor antagonists, when taken with food, may be reduced by the presence of food in the stomach.

Food is digested in the stomach, by mixing with digestive aids such as secreted acid and digestive enzymes, to form a material referred to as chyme. Chyme is a thick semifluid mass of partly digested food that is passed from the stomach to the duodenum The present invention provides a means for allowing the active drug to remain in the stomach in the presence of food. By this means, food is converted in the stomach to chyme and emptied into the duodenum prior to transfer of the active drug into the duodenum. The active drug is transferred to the duodenum only after food has first been converted into chyme and passed into the duodenum. The active drug is thus released in the intestine following food digestion, thereby preventing food interaction.

SUMMARY OF THE INVENTION

The invention is an oral, coated pharmaceutical composition suitable for administration to a patient. The coated compositions comprise an active drug, suitable solid oral dosage form pharmaceutical excipients, and a suitable protective enteric coating surrounding the active drug and pharmaceutical excipients. The suitable coating prevents release from the composition of active drug while the coated composition is located in the stomach, and provides for release of the active drug following transfer of the composition from the stomach to the intestine.

The compositions have sufficient effective diameter to prevent gastric emptying of the composition from the stomach into the duodenum until gastric emptying of chyme from the stomach is completed.

The compositions are specifically designed to prevent interaction of the active drug with food. While the compositions remain in the stomach, food is converted in the stomach to chyme and then transported to the duodenum. Only after gastric emptying of the chyme does the composition leave the stomach and enter the duodenum. The active drug is then released from the coated composition into the intestine.

The compositions include a coated medicament having releasability of the active drug only in the intestine having an inner core and an outer coating, wherein the inner core comprises active drug and one or more suitable pharmaceutically acceptable excipients, and wherein the outer coating does not substantially dissolve in the stomach and does substantially dissolve in the intestine.

The invention also includes a method for preventing interaction between food and an active drug whose absorption is affected by the presence of food, which comprises administering to the patient an oral, coated pharmaceutical composition of the invention which releases the active drug into the intestine after food has been digested.

The active drug can be a fibrinogen receptor antagonist suitable for administration to a patient in need of therapy for inhibiting platelet aggregation. The coated compositions of the invention thus may comprise an inhibitor of fibrinogen binding to the GP IIb/IIIa receptor, suitable solid oral dosage form pharmaceutical excipients, and a suitable protective enteric coating surrounding the inhibitor and pharmaceutical excipients. The suitable coating prevents release from the composition of the fibrinogen receptor antagonist while the coated composition is located in the stomach, and provides for release of the fibrinogen receptor antagonist following transfer of the composition from the stomach to the intestine. This only occurs after the food has been digested and eliminated from the stomach.

The invention also includes the use of a composition of the invention in the manufacture of a medicament for reducing the risk of acute coronary ischemic syndrome in patients at risk to acute coronary ischemic syndrome, in a mammal.

The compositions are particularly useful for reducing the risk of acute coronary ischemic syndrome in patients at risk to acute coronary ischemic syndrome. The compositions minimize the risk associated with oral fibrinogen receptor antagonists that interact with food, and provide a safer means for treating patients in need of fibrinogen receptor antagonists.

The invention also includes a composition in the manufacture of a medicament for preventing, in a patient, interaction between food and an active drug, the absorption rate of which drug is substantially affected by the coinciding presence of food in the stomach.

DETAILED DESCRIPTION OF THE INVENTION

The invention is an oral drug dosage unit, for administration to a patient, having active drug, and an effective diameter and surface composition sufficient for the unit to be transported from the stomach into the duodenum following substantially complete emptying of chyme from the stomach into the duodenum and prior to release of active drug from the unit, wherein the active drug has an absorption rate that is affected by the coinciding presence of food in the stomach, the effective diameter of the unit prevents gastric emptying of the unit prior to gastric emptying of chyme, and the surface composition is an enteric coating which prevents release of the active drug in the stomach and allows release of the active drug in the intestine.

Active drugs having food interaction are those where drug absorption is affected by the presence of food, to such an extent that the medicinal benefit ordinarily provided by the drug (in the absence of food) is detrimentally altered.

Compositions within the scope of the invention, having releasability of the active drug only in the intestine, have an inner core and an outer enteric coating, wherein the inner core comprises an active drug and one or more suitable pharmaceutically acceptable excipients, and wherein the outer coating does not substantially dissolve in the stomach and does substantially dissolve in the intestine.

The invention also includes a method for preventing, in a patient, interaction between food and an active drug, the absorption rate of which drug is substantially affected by the coinciding presence of food in the stomach, which comprises administering to the patient an oral drug dosage unit having the active drug, an effective diameter sufficient for the unit to be transported from the stomach into the duodenum following substantially complete emptying of chyme from the stomach into the duodenum and prior to release of active drug from the unit, and an enteric coating surface composition which retains the active drug in the stomach and releases the active drug in the intestine.

In the compositions of the invention, the coating which delays release of the active drug is insoluble in pH environments such as those in the stomach, e.g. less than 4, but soluble in pH environments such as those in the intestine, e.g. about 5.5. or greater.

The effective diameter of the pharmaceutical composition of the invention is between about 3 mm and 20 mm, preferably between about 6 and 15 mm, e.g. 7, 8, 9, 10, 11, 12, 13, and 14 mm. "Effective diameter" for purposes of this invention refers to the dimension of the composition that is presented to the opening between the stomach and the duodenum and which limits entry of the composition into the duodenum. For example, the effective diameter of a spheroid is the diameter of the spheroid. The effective diameter of a tablet is the diameter of the tablet face. The effective diameter of a cylindrical capsule is the diameter of the narrow dimension of the cylinder.

The compositions of the present invention may be prepared in any of a number of ways as long as the objective of preventing release of the active drug in the stomach and providing for release of the active drug in the intestine is achieved. Such compositions are prepared with enteric coatings that are insoluble in gastric juices but readily soluble on passage into the intestine.

Compositions of the invention may also be prepared by mixing the active drug with an excipient, and coating the mixture with a thin polymer film. For example, the active drug is mixed with microcrystalline cellulose to form a spheroid which is then coated with a film of hydroxypropyl methyl cellulose phthalate which may or may not contain a plasticizer which prevents any release of the drug in the stomach. When the composition reaches the intestine, the active drug is released.

Compositions of the invention may also be prepared by mixing the active drug and an acid such as fumeric or tartaric acid which is compressed into a tablet or capsule shape and coated with lacquers that are insoluble in gastric juices and soluble in intestinal juices. Compositions of the invention may also be prepared by mixing the active drug with materials for forming a gel capsule, inserting drug particles into a capsule, or inserting a liquid drug formulation into a capsule, which capsules are then coated with lacquers that are insoluble in gastric juices and soluble in intestinal juices. These lacquers include copolymers of acrylic acid and methacrylic acid esters. The acidic matrix prevents quick dissolution early and yet promotes the drugs' bioavailability further downstream in the digestive tract.

Compositions of the invention may also be prepared by coating a solid dosage form of the active drug with hydroxypropyl methyl cellulose phthalate or acidic succinyl and acetyl esters of hydroxypropyl methyl cellulose. Triethylcitrate is added as a plasticizer which aids in the binding of the coating material to the core pellet. The coating resists dissolution in the stomach but completely dissolves in the small intestine.

Suitable materials for providing enteric coatings include, for example, hydroxypropyl methyl cellulose phthalate, hydroxypropylmethyl cellulose acetate succinate, hydroxypropyl methyl cellulose phthalate, hydroxypropyl methyl cellulose hexahydrophthalate, shellac, cellulose acetate, cellulose acetate phthalate, polyvinyl acetate phthalate, carboxymethyl ethyl cellulose, methacrylic acid copolymers, methacrylic ester copolymers and the like. A commercially available enteric coating system (Sureteric YAE-6-18107), which contains polyvinyl acetate phthalate, talc, polyethylene glycol, titanium dioxide, sodium bicarbonate, triethyl citrate, purified stearic acid, sodium alginate, and colloidal silicon dioxide, may be used.

In general, solid dosage forms comprising the active drug may be coated using conventional coating techniques such as conventional pan coating techniques or column spray coating techniques.

For example, coating pans, e.g. subglobular, pear shaped or hexagonal pans, which are inclined are set to rotate at an appropriate setting sufficient to allow uncoated tablets to be exposed to spray solutions of the polymer used to form the coat. The pan is heated to a sufficient temperature to allow the coat to dry soon after contact with the outside of the tablet.

Some pans have a cylindrical shape, are rotated horizontally, and have at least some regions of the walls perforated by small holes or slots. This design permits a one-way air flow through the pan. In other designs the flow of air is through the tablet bed and out through the perforated wall of the pan. In others the air flows from the perforated pan wall through the tablet bed into the central region, i.e., countercurrent to the coating spray direction. Still others permit either co- or counter-current air flow to suit particular products.

The coating is sprayed in one of several methods. One method relies entirely on hydraulic pressure to produce a spray when material is forced through a nozzle (airless spraying). In another method, atomization of the spray is assisted by turbulent jets of air. This method tends to produce a more easily controlled spray pattern and is therefore better for small-scale operations, although both are capable of giving the flat jet profile preferred for pan operation.

The thickness of coating required on the granules depends on the dissolution profile of the particular coating materials. The coating can contain a plasticizer and possibly other coating additives such as coloring agents, gloss producers, talc and/or magnesium stearate.

Active drugs useful in the present invention include fibrinogen receptor antagonists such as those described in U.S. Pat. Nos. 5,470,849, 5,463,011, 5,455,243, 5,451,578, 5,446,056, 5,441,952, 5,422,249, 5,416,099, 5,405,854, 5,397,791, 5,393,760, 5,389,631, 5,380,713, 5,374,622, 5,358,956, 5,344,783, 5,340,798, 5,338,723, 5,334,596, 5,321,034, 5,318,899, 5,312,923, 5,294,616, 5,292,756, 5,281,585, 5,272,158, 5,264,420, 5,260,307, 5,239,113 (e.g. Ethyl 3-[[4-[[4-(aminoiminomethyl)phenyl]amino]-1,4-dioxobutyl]amino]-4-pentynoate), U.S. Pat. No. 5,227,490, 5,206,373, 4,703,036 (e.g. N-Methyl-D-phenylalanyl-N-[(1S)-1-formyl-4-guanidinobutyl]-L-prolinamide), EP 505 868 (e.g. ((1-(2-((4-(aminoiminomethyl)benzoyl)amino)-3-(4-hydroxyphenyl)-1-oxopropyl)-4-piperidinyl)oxy)-(S)-acetic acid) WO 9311152 (e.g. N-(2-(2-(((3-((aminoiminomethyl)amino)propyl)amino)-carbonyl)-1-piperidinyl)-1-(cyclohexylmethyl)-2-oxoethyl)-(R,S)-glycine), (R)-methyl-3-[[[3-[4 -(aminoiminomethyl) phenyl]-4,5-dihydro-5-isoxazolyl]acetyl]amino]-N-(butoxycarbonyl)-L-alanine monoacetate, EP 333 356, and WO 9422820. They are described as useful for inhibiting fibrinogen binding and inhibiting clot formation.

Glycoprotein IIb/IIIa receptor antagonists and their pharmaceutically acceptable salts are useful in the present invention. The term "pharmaceutically acceptable salts" means non-toxic salts of the compounds which include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Pharmaceutically effective amounts of the glycoprotein IIb/IIIa receptor antagonists are suitable for use in the compositions and methods of the present invention. The term "pharmaceutically effective amount" means that amount of a drug or pharmaceutical agent that will elicit the biological or medical response of a tissue, system or animal that is being sought by a researcher or clinician.

The methods of the present invention are useful in combination with procedures for treating patients with other anticoagulants (e.g. heparin and warfarin), thrombolytic agents (e.g. streptokinase and tissue plasminogen activator), and platelet antiaggregation agents (e.g. aspirin and dipyridamole).

In accordance with the invention, glycoprotein IIb/IIIa receptor antagonists can be administered to the patient in one oral composition, such as a tablet or capsule, or in several oral compositions.

Suitable oral compositions include tablets, compressed capsules, gel capsules containing drug integrated into the gel matrix forming the gel capsule, gel capsules containing drug particles, or gel capsules containing liquid drug composition (each of which may include sustained release or timed release formulations), which are coated with an enteric coating. The coated composition may be a tablet comprising the active drug with other excipients and an enteric coat, a non-tablet solid complex comprising the active drug with other excipients and an enteric coat contained in a capsule (e.g. wherein the non-tablet solid complex is loaded into the capsule) which is coated with an enteric coat, or other form, with the condition being that the active drug is protected from release in the stomach but not from release in the intestine.

The active drug may be administered to patients where prevention of thrombosis by inhibition of binding of fibrinogen to the platelet membrane glycoprotein complex IIb/IIIa receptor is desired. Such administration is useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. The active drugs may be administered to these surgical patients to prevent the formation of thrombi and thromboemboli.

Other applications include prevention of platelet thrombosis, thromboembolism and reocclusion during and after thrombolytic therapy and prevention of platelet thrombosis, thromboembolism and reocclusion after angioplasty or coronary artery bypass procedures. The methods may also be used to prevent myocardial infarction.

The dosage regimen utilizing the active drug is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of active drug when used for the indicated effects, will range between about 0.005 mg per kg of body weight per day (mg/kg/day) to about 50 mg/kg/day and preferably 0.005–20 mg/kg/day and most preferably 0.005–10 mg/kg/day. Suitable oral tablets contain between 0.1 mg and 500 g, preferably between 1.0 mg and 250 g, most preferably between 1.0 mg and 150 g, e.g. 1 mg, 50 mg, 100 mg, 150 mg, 250 mg, or 500 mg. Oral administration may be in one or divided doses of two, three, or four times daily.

The active drug can be administered in admixture with suitable pharmaceutical diluents, excipients or carriers (collectively referred to herein as "carrier" materials) suitably selected with respect to the intended form of administration, that is, oral tablets, capsules, and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, microcrystalline cellulose, magnesium stearate, dicalcium phosphate, calcium sulfate, mannitol, sorbitol and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, stearic acid, sodium benzoate, sodium acetate, sodium chloride and the like. Disintegrants include, without limitation, starch and derivatives thereof, microcrystalline cellulose, methyl cellulose, agar, bentonite, croscarmellose sodium, xanthan gum and the like.

Therapeutic Treatment

The compositions are useful for treating patients where inhibition of human or mammalian platelet aggregation or adhesion is desired. They are useful in surgery on peripheral arteries (arterial grafts, carotid endaterectomy) and in cardiovascular surgery where manipulation of arteries and organs, and/or the interaction of platelets with artificial surfaces, leads to platelet aggregation and potential formation of thrombi and thromboemboli. Methods of the invention may be used to prevent the formation of thrombi and thromboemboli.

The present invention is demonstrated in a study of patients with acute coronary ischemic syndromes who are undergoing early coronary revascularization with percutaneous coronary angioplasty or atherectomy. Because of unstable plaque with thrombus, percutaneous revascularization procedures in these patients carry with them considerable higher morbidity than procedures performed in patients with stable coronary disease. All patients receive heparin (a standard PTCA regimen, weight adjusted in lighter patients) and aspirin. Heparin is discontinued after completion of the procedure and sheaths removed when the heparin-effect has dissipated. The compositions are administered to patients who are evaluated at 30 days for acute coronary ischemic syndrome and the need for follow-up intervention associated with acute coronary ischemic syndrome, including coronary artery bypass grafting, repeat percutaneous intervention for acute ischemia, and insertion of a coronary endovascular stent.

EXAMPLE 1 gp IIb/IIIa Antagonist Treatment (Oral)

Patients with acute coronary ischemic syndromes receive coronary revascularization with angioplasty. Aspirin is administered in a dose of 325 mg at least two hours before angioplasty, and daily thereafter. Heparin is given intravenously in an initial bolus dose of 10,000 to 12,000 units followed by incremental bolus doses of up to 3000 units at 15-minute intervals, but no more than 20,000 units is given during the procedure. The goal is to keep the activated clotting time between 300 and 350 seconds during the operation. Heparin is continued by constant infusion for at least 12 hours to maintain the activated partial-thromboplastin time at 1.5 to 2.5 times the control value. Aspirin is required at discharge in a dose of 325 mg per day.

Patients receive an oral tablet, as prepared in Example 2, containing 15 mg of the fibrinogen receptor gp IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid (compound 1-1), described in WO 94/18981.

Patients are monitored 30 days following initiation of the fibrinogen receptor gp IIb/IIIa antagonist infusion, and show reduction in acute coronary ischemic syndrome after 30 days.

EXAMPLE 2

Tablet Preparation

Coated tablets containing 15 mg of the fibrinogen receptor gp IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a] [1,4]diazepin-2-yl]carbonyl]-amino]propionic acid (compound 1–1) are prepared as illustrated below:

Tablet for doses containing 15 mg of the gp IIb/IIIa receptor antagonist

| Ingredient | mg |
| --- | --- |
| 1–1 | 15.0 |
| Microcrystalline cellulose | 42.2 |
| Dicalcium phosphate | 42.2 |
| Croscarmellose sodium | 0.1 |
| Magnesium stearate | 0.5 |
| Hydroxypropyl methyl cellulose phthalate | 10 |

Compound 1-1, microcrystalline cellulose, dicalcium phosphate and croscarmellose sodium are mixed and then lubricated with magnesium stearate and the resulting mixture is then compressed into tablets having diameter of 8 mm. The tablets are coated in a coating pan with hydroxypropyl methyl cellulose phthalate in a coating amount of 10 mg per tablet.

EXAMPLE 3

Tablet Preparation

Coated tablets containing 15 mg of the fibrinogen receptor gp IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid (compound 1–1) are prepared as illustrated below:

Tablet for doses containing 15 mg of the gp IIb/IIIa receptor antagonist

| Ingredient | mg |
| --- | --- |
| 1-1 | 15.0 |
| Microcrystalline cellulose | 200.0 |
| Modified food corn starch | 8.5 |
| Magnesium stearate | 1.5 |
| Hydroxypropyl methyl cellulose phthalate | 20.0 |

Compound 1-1, microcrystalline cellulose, and a portion of the corn starch are mixed and granulated into 10% corn starch paste. The resulting granulation is sieved, dried and blended with the remainder of the corn starch and the magnesium stearate. The resulting granulation is then compressed into tablets having diameter of 8 mm. The tablets are coated in a coating pan with hydroxypropyl methyl cellulose phthalate in a coating amount of 20 mg per tablet.

EXAMPLE 4

Capsule Preparation

Capsules containing the fibrinogen receptor gp IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid (compound 1-1) are prepared as illustrated below:

| Ingredient | mg |
| --- | --- |
| 1-1 | 15.0 |
| Microcrystalline cellulose | 42.2 |
| Dicalcium phosphate | 42.2 |
| Croscarmellose sodium | 0.1 |
| Magnesium stearate | 0.5 |
| Hydroxypropyl methyl cellulose phthalate | 10 |

Compound 1-1, microcrystalline cellulose, disodium phosphate and croscarmellose sodium are mixed in a blender. The resulting mixture is granulated and dried prior to milling. Milled granules are lubricated and filled into a standard pharmaceutical capsule, having a narrow dimension of 4 mm, which is then coated with hydroxypropyl methyl cellulose phthalate.

EXAMPLE 5

Tablet Preparation

Tablets containing the fibrinogen receptor gp IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid (compound 1-1) are prepared as illustrated below.

Tablet core components

| Ingredient | mg |
| --- | --- |
| 1-1 | 1.0 |
| Microcrystalline cellulose | 146.42 |
| Calcium phosphate dibasic | 146.42 |
| Croscarmellose sodium | 4.5 |
| Magnesium stearate | 1.5 |

Compound 1-1, microcrystalline cellulose, calcium phosphate dibasic, croscarmellose sodium were combined in a conventional manner to form the core tablet. Tablets were then coated with a pre-coat solution of 2.4 mg hydroxypropylmethylcellulose, 2.4 mg hydroxypropylcellulose, 0.96 mg titanium dioxide, and 60 microliters of water. After the pre-coat solution was applied, the enteric coat was added The enteric coat was made using Colorcon's Sureteric TAE-6-18107 aqueous based enteric coating system. A 15% solution of Sureteric was made by suspending the powder in water. Dow Corning's antifoam AF emulsion was added to prevent foaming (weight equal to 0.334% of the weight of the Sureteric in the suspension). The solution was added until a 10% weight gain (based on core tablet weight of 300 mg) was achieved.

EXAMPLE 6

The tablet prepared in Example 5 was prepared. After the enteric coating was applied, an additional pre-coat solution of 2.4 mg hydroxypropylmethylcellulose, 2.4 mg hydroxypropylcellulose, 0.96 mg titanium dioxide, and 60 microliters of water was added to achieve a 3% weight gain.

What is claimed is:

1. An oral dosage unit, for administration to a patient, having a therapeutically effective amount of a fibrinogen receptor antagonist, and an effective diameter and surface composition sufficient for the oral drug dosage unit to be transported from the stomach into the duodenum following substantially complete emptying of chyme from the stomach into the duodenum and prior to release of fibrinogen receptor antagonist from the oral drug dosage unit, wherein:

a) the fibrinogen receptor antagonist has an absorption rate that is affected by the coinciding presence of food in the stomach;

b) the effective diameter of the oral drug dosage unit prevents gastric emptying of the oral drug dosage unit prior to gastric emptying of chyme; and c) the surface composition is an enteric coating which prevents release of the fibrinogen receptor antagonist in the stomach and allows release of the fibrinogen receptor antagonist in the intestine, wherein the fibrinogen receptor antagonist is selected from the group consisting of 2(S)-[(p-Toluenesulfonyl) amino]-3-[[[5,6,7,8-tetrahydro-4-oxo-5-[2-(piperidin-4-yl)ethyl]-4H -pyrazolo-[1,5-α][1,4]diazepin-2-yl] carbonyl]amino]propionic acid, (R)-methyl-3-[[3-[4-(aminoiminomethyl)phenyl]-4,5-dihydro-5-isoxazolyl] acetyl]amino]-N-butoxycarbonyl)-L-alanine monoacetate and Ethyl 3-[[4-[[4-(aminoiminomethyl) phenyl]amino]-1,4-dioxobutyl]amino-4-pentynoate and pharmaceutically acceptable salts thereof.

2. An oral drug dosage unit of claim 1 wherein the effective diameter of the oral drug dosage unit is between about 3 mm and 20 mm.

3. An oral drug dosage unit of claim 1 having releasability of the fibrinogen receptor antagonist only in the intestine having an inner core and an outer enteric coating, wherein the inner core comprises a fibrinogen receptor antagonist and one or more suitable pharmaceutically acceptable excipients, and wherein the outer coating does not substantially dissolve in the stomach and does substantially dissolve in the intestine.

4. An oral drug dosage unit of claim 3 wherein the outer coating comprises one or more polymers which are insoluble in pH environments in the stomach and soluble in pH environments in the intestine.

5. An oral drug dosage unit of claim 4 wherein the polymers are selected from the group consisting of hydroxypropyl methyl cellulose phthalate, hydroxypropylmethyl cellulose acetate succinate, hydroxypropyl methyl cellulose hexahydrophthalate, cellulose acetate phthalate, carboxymethyl ethyl cellulose, and methacrylic acid.

6. An oral drug dosage unit of claim 3, wherein the fibrinogen receptor antagonist is 2(S)-[(p-Toluenesulfonyl) amino]-3-[[[5,6,7,8-tetrahydro-4-oxo-5-[2-(piperidin-4-yl) ethyl]-4H-pyrazolo-[1,5-a][1,4]diazepin-2-yl]carbonyl]-amino]propionic acid and pharmaceutically acceptable salts thereof.

7. A method for reducing the risk of acute coronary ischemic syndrome in patients at risk to acute coronary ischemic syndrome, comprising administering to the patient an oral drug dosage unit of claim 1.

8. A method for preventing, in a patient, interaction between food and a therapeutically effective amount of a fibrinogen receptor antagonist, the absorption rate of which fibrinogen receptor antagonist is substantially affected by the coinciding presence of food in the stomach, which comprises administering to the patient an oral drug dosage unit having the fibrinogen receptor antagonist, an effective diameter sufficient for the oral drug dosage unit to be transported from the stomach into the duodenum following substantially complete emptying of chyme from the stomach into the duodenum and prior to release of fibrinogen receptor antagonist from the oral drug dosage unit, and an enteric coating surface composition is an enteric coating which prevents release of the fibrinogen receptor antagonist in the stomach and allows release of the active drug in the intestine.

* * * * *